(12) United States Patent
Kawabata

(10) Patent No.: US 8,453,524 B2
(45) Date of Patent: Jun. 4, 2013

(54) SOLUTION FEEDING DEVICE

(75) Inventor: Katsuhiko Kawabata, Kunitachi (JP)

(73) Assignee: IAS Inc., Toyko (JP)

( * ) Notice: Subject to any disclaimer, the term of this patent is extended or adjusted under 35 U.S.C. 154(b) by 830 days.

(21) Appl. No.: 11/997,249

(22) PCT Filed: Aug. 14, 2006

(86) PCT No.: PCT/JP2006/316004
§ 371 (c)(1),
(2), (4) Date: Jul. 23, 2010

(87) PCT Pub. No.: WO2007/023705
PCT Pub. Date: Mar. 1, 2007

(65) Prior Publication Data
US 2010/0276019 A1    Nov. 4, 2010

(30) Foreign Application Priority Data
Aug. 25, 2005  (JP) ................. 2005-244110

(51) Int. Cl.
| | |
|---|---|
| *G01N 1/38* | (2006.01) |
| *F04B 23/02* | (2006.01) |
| *F04B 23/10* | (2006.01) |
| *F04B 49/00* | (2006.01) |
| *F04B 49/22* | (2006.01) |
| *G01N 35/10* | (2006.01) |
| *F04B 23/14* | (2006.01) |

(52) U.S. Cl.
CPC .............. *G01N 1/38* (2013.01); *G01N 35/1009* (2013.01); *G01N 35/1065* (2013.01); *F04B 23/02* (2013.01); *F04B 23/10* (2013.01); *F04B 23/14* (2013.01); *F04B 49/22* (2013.01)
USPC ........ 73/863; 73/61.59; 73/64.56; 73/864.34; 73/864.81; 137/565.11; 137/565.33; 137/605; 137/897

(58) Field of Classification Search
CPC ....... G01N 1/38; G01N 35/10; G01N 35/1009; G01N 35/1065; G01N 2001/38; G01N 2001/383; G01N 2001/386; G01N 2030/047; G01N 2035/00514; G01N 2035/00584; G01N 2035/00693; G01N 2035/1009; F04B 23/02; F04B 23/04; F04B 23/10; F04B 23/14; F04B 49/00; F04B 49/22
USPC .................. 73/1.02–1.03, 1.05, 61.55–61.56, 73/61.59, 64.56, 863–863.03, 864.22, 73/864.34–864.35, 864.81, 864.85; 137/565.11, 137/565.23, 565.29, 565.33, 605, 896–897
See application file for complete search history.

(56) References Cited

U.S. PATENT DOCUMENTS

| | | | |
|---|---|---|---|
| 3,627,494 A | * | 12/1971 | Fahnrich |
| 3,712,795 A | * | 1/1973 | Atkinson et al. |
| 4,258,564 A | * | 3/1981 | Hulme et al. ............ 73/61.55 X |
| 4,294,127 A | * | 10/1981 | Tomoff ....................... 73/864.21 |
| 4,318,884 A | * | 3/1982 | Suzuki ............................ 422/63 |
| 4,577,517 A | * | 3/1986 | Knight ....................... 73/864.81 |
| 4,849,110 A | * | 7/1989 | Takata et al. ............ 73/61.55 X |
| 5,243,847 A | * | 9/1993 | Engeljehringer et al. |
| 5,277,871 A | * | 1/1994 | Fujii et al. ....................... 422/70 |
| 5,308,774 A | * | 5/1994 | Miura et al. .................... 436/87 |
| 5,646,727 A | | 7/1997 | Hammer et al. |
| 5,783,450 A | * | 7/1998 | Yoshida et al. ............... 436/161 |
| 6,295,864 B1 | * | 10/2001 | You et al. ................. 73/61.55 X |
| 2010/0061891 A1 | * | 3/2010 | Saito et al. ................... 422/68.1 |

FOREIGN PATENT DOCUMENTS

| | | | | |
|---|---|---|---|---|
| EP | 225115 A | * | 6/1987 | |
| EP | 220666 B | * | 1/1992 | |
| EP | 514678 A1 | * | 11/1992 | |
| EP | 1203959 A1 | * | 5/2002 | |
| EP | 1517147 A2 | * | 3/2005 | |
| JP | 59027246 A | * | 2/1984 | |
| JP | 2001-249139 | | 9/2001 | |
| JP | 2002-350315 | | 12/2002 | |
| WO | WO 9402945 A1 | * | 2/1994 | |
| WO | WO 2004/017046 | | 2/2004 | |

OTHER PUBLICATIONS

English Translation of International Preliminary Report on Patentability for PCT/JP2006/316004, issued Feb. 26, 2008, 4 pages.*

* cited by examiner

Primary Examiner — Thomas P Noland
(74) Attorney, Agent, or Firm — Finnegan, Henderson, Farabow, Garrett & Dunner, L.L.P.

(57) ABSTRACT

A solution feeding device for feeding a sample solution which is precisely adjusted in the mixed quantity of a standard solution is realized. The solution feeding device comprises: a mixing module (100) including a first passage (101), a second passage (102), and a third passage (103) for providing communications of the midways of those two passages with a higher passage resistance than those of the two passages; a first storage unit (10) communicating with one end side of the first passage for storing a sample solution; a suctioning nebulizer (20) communicating with the other end side of the first passage for sucking the sample solution; a second storage unit (30) communicating through an on-off valve (31) with one end side of the second passage for storing a standard solution; and a syringe pump (40) communicating with the other end side of the second passage for sucking and discharging the standard solution, respectively, in the open state and the closed state of the on-off valve.

3 Claims, 3 Drawing Sheets

SOLUTION FEEDING DEVICE

TECHNICAL FIELD

The present invention relates to a solution feeding device and, more particularly, to a device for feeding a mixed liquid of a sample solution and a standard solution to a mass spectrometer, an optical emission spectrometer or the like.

BACKGROUND ART

The mass spectrometer, the optical emission spectrometer or the like may mix the standard solution into the sample solution for analyses. In case the mixing of the standard solution is on-line performed, a peristaltic pump is used. The sample solution containing the standard solution is injected into the analyzing device through a nebulizer (as referred to Patent Document 1).

Patent Document 1: U.S. Pat. No. 5,646,727

DISCLOSURE OF THE INVENTION

Problems that the Invention is to Solve

The mixed quantity of the standard solution into the sample solution has to be precisely adjusted, but the peristaltic pump is of the type, in which a tube is squeezed by a roller thereby to pump the liquid. It is, therefore, difficult to adjust the mixing rate of the standard solution precisely.

Therefore, an object of the present invention is to realize a solution feeding device for feeding a sample solution which is precisely adjusted in the mixed quantity of a standard solution.

Means for Solving the Problems

In order to solve the aforementioned problems, according to the present invention, there is provided a solution feeding device characterized by comprising: mixing means including a first passage, a second passage, and a third passage for providing communications of the midways of those two passages with a higher passage resistance than those of the two passages; first storage means communicating with one end side of the first passage of said mixing means for storing a sample solution; suction means communicating with the other end side of the first passage of said mixing means for sucking the sample solution; second storage means communicating through an on-off valve with one end side of the second passage of said mixing means for storing a standard solution; and a syringe pump communicating with the other end side of the second passage of said mixing means for sucking and discharging the standard solution, respectively, in the open state and the closed state of the on-off valve.

It is preferred for making the mixed quantity of the standard solution proportional to the flow rate of the sample solution that the aforementioned solution feeding device comprises detecting means for detecting the flow rate of the sample solution, and control means for controlling said syringe pump on the basis of the detection signal of said detecting means.

It is preferred for easy grasping the suction state of the sample solution that the aforementioned solution feeding device comprises monitor means for monitoring the detection signal of said detecting means.

Advantage of the Invention

According to the present invention, the solution feeding device comprises: mixing means including a first passage, a second passage, and a third passage for providing communications of the midways of those two passages with a higher passage resistance than those of the two passages; first storage means communicating with one end side of the first passage of said mixing means for storing a sample solution; suction means communicating with the other end side of the first passage of said mixing means for sucking the sample solution; second storage means communicating through an on-off valve with one end side of the second passage of said mixing means for storing a standard solution; and a syringe pump communicating with the other end side of the second passage of said mixing means for sucking and discharging the standard solution, respectively, in the open state and the closed state of the on-off valve. As a result, the solution feeding device can feed the sample solution which is precisely adjusted in the mixed quantity of the standard solution.

Figure 1:
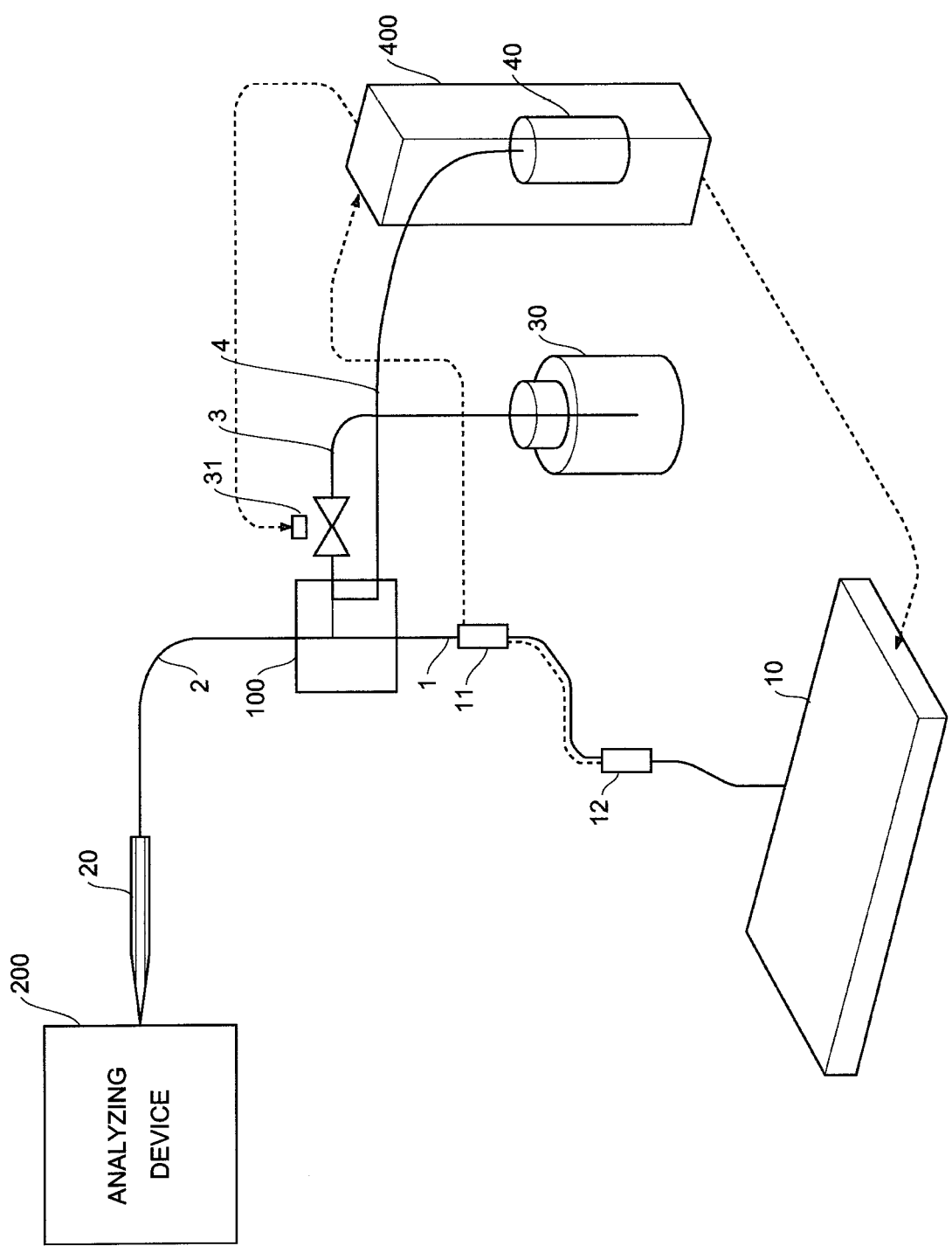
[FIG. 1] A diagram schematically showing a constitution of a solution feeding device of one example of the best mode for executing the present invention.

DESCRIPTION OF REFERENCE NUMERALS AND SIGNS 1, 2, 3 and 4: Tube
10: Sample Solution Storage Unit
11 and 12: Flow Rate Sensor
20: Nebulizer
30: Internal Standard Solution Storage Unit
31: On-Off Valve
40: Syringe Pump
100: Mixing Module
101, 102 and 103: Passage
200: Analyzing Device
400: Control Module
401: Controller
402: Monitor

BEST MODE FOR CARRYING OUT THE INVENTION

The best mode for carrying out the invention is described in detail in the following with reference to the accompanying drawings. Here, the present invention should not be limited to the best mode for carrying out the invention. The constitution of a solution feeding device is schematically shown in FIG. 1. The present device is one example of the best mode for carrying out the invention. The constitution of the present device exemplifies one example of the best mode for carrying out the invention relating to the solution feeding device.

As shown in FIG. 1, the present device includes a mixing module 100. This mixing module 100 has four ports. These ports communicate via internal passages. Tubes 1, 2, 3 and 4 are individually connected at their ends with the four ports. Here, the tube 3 is connected through an on-off valve 31.

The other end of the tube 1 is connected with a sample solution storage unit 10. As a result, the tube 1 acts as a sample solution inflow tube. The other end of the tube 2 is connected with a nebulizer 20. As a result, the tube 2 acts as a sample solution outflow tube. Here, the internal standard solution is so mixed into the sample solution in the tube 2 as will be described hereinafter.

The nebulizer 20 injects the sample solution into an analyzing device 200. This analyzing device 200 is exemplified by an inductively coupled plasma mass spectrometer (ICP-MS), a liquid chromatography mass spectrometer (LC-MS) or an inductively coupled plasma optical emission spectrometer (ICP-OES).

The other end of the tube 3 is connected with an internal standard solution storage unit 30. As a result, the tube 3 acts as an internal standard solution inflow tube. The other end of the tube 4 is connected with a syringe pump 40. As a result, the tube 4 acts as an internal standard solution inflow/outflow tube.

The syringe pump 40 is disposed in a control module 400. The control module 400 mounts the later-described controller therein. To the control module 400, there are inputted the detection signals of two flow rate sensors 11 and 12 disposed along the tube 1. The control module 400 controls the syringe pump 40 with an output signal. The control module 400 further controls the on-off valve 31 and the not-shown autosampler belonging to the sample solution storage unit 10.

Figure 2:
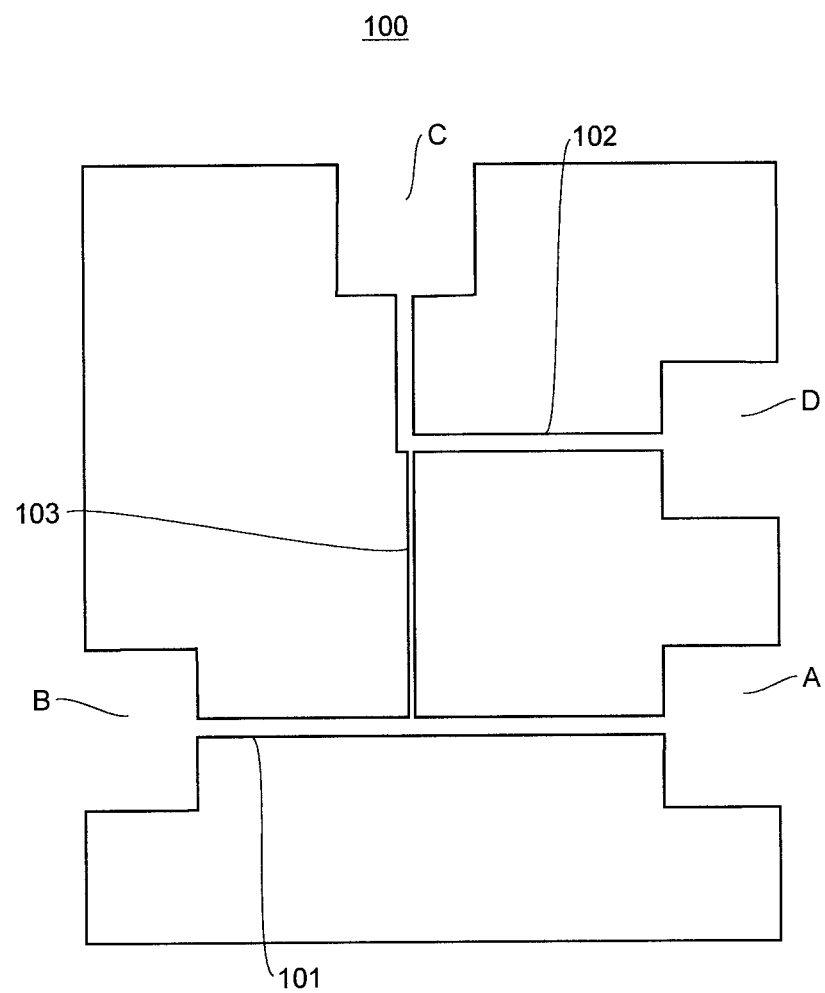
[FIG. 2] A diagram showing an internal constitution of a mixing module.

FIG. 2 is a sectional diagram showing the detailed constitution of the mixing module 100. As shown in FIG. 2, the mixing module 100 has four ports A, B, C and D. The tubes 1, 2, 3 and 4 are connected to those ports A, B, C and D, respectively.

The mixing module 100 has passages 101, 102 and 103 therein. The passage 101 is a straight passage to provide communications between the port A and the port B. As a result, the passage 101 acts as a passage for the sample solution. The passage 102 is a passage bent at right angles to provide communications between the port C and the port D. As a result, the passage 102 acts as a passage for the internal standard solution. The passage 103 is a straight passage to provide communications between the passage 101 and the passage 102. As a result, the passage 103 acts as a passage for connecting the sample solution passage and the internal standard solution passage.

The individual passages are sized such that: the passage 101 has an internal diameter of 0.5 mm and an entire length of 20 mm; the passage 102 has an internal diameter of 0.75 mm and an entire length of 15 mm; and the passage 103 has an internal diameter of 0.1 mm and an entire length of 10 mm. Of the entire length of 15 mm of the passage 102, the portion bent at right angles toward the port C is 5 mm, and the remainder is 10 mm.

In this passage constitution, the passage resistance to the flow of the solution is far higher in the passage 103 than in the passage 101 and the passage 102. In other words, the sample solution passage and the internal standard solution passage are connected by the passage having the high passage resistance.

Figure 3:
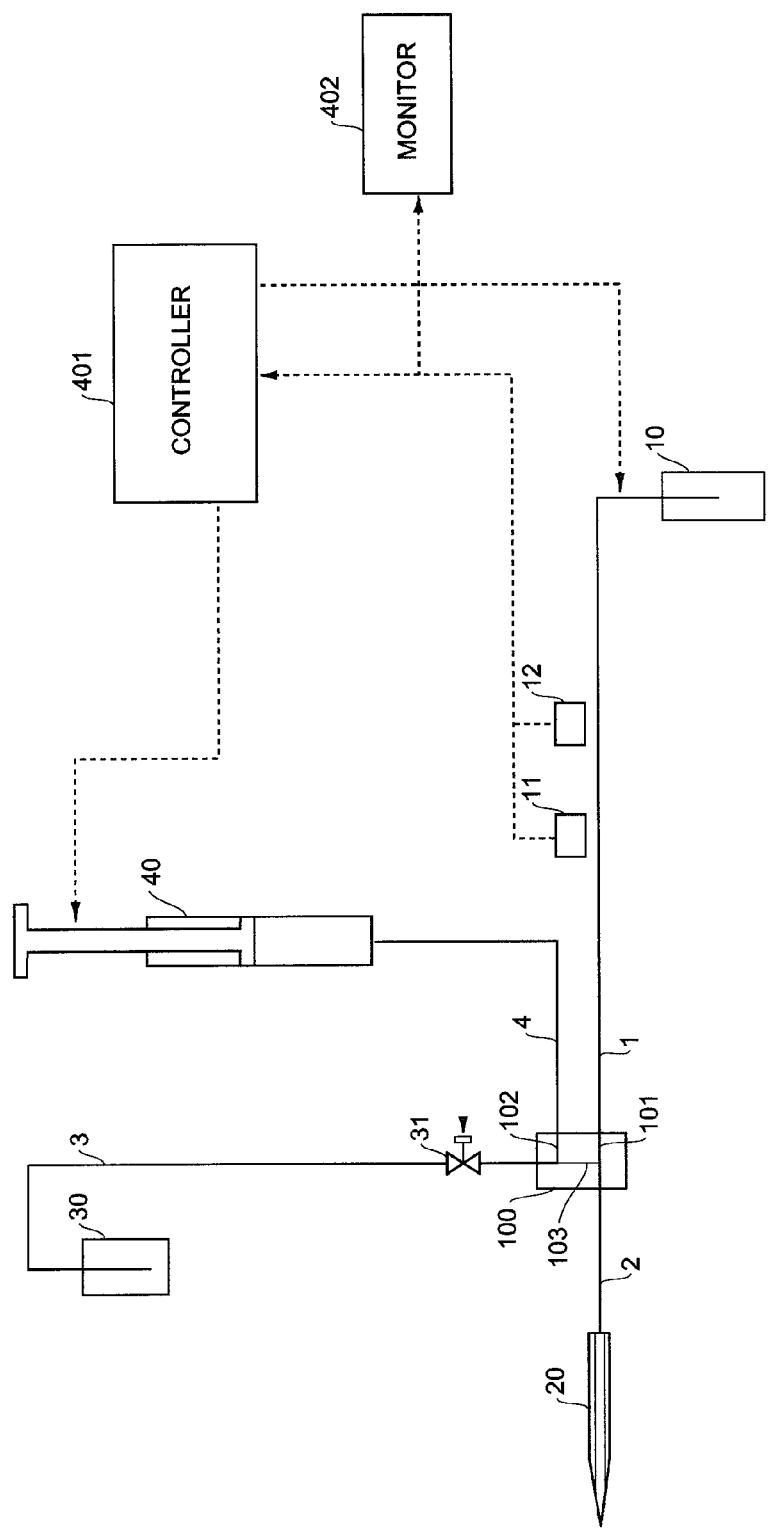
[FIG. 3] A diagram showing a system of solution passages.

FIG. 3 shows a system diagram of the solution passages in the present device. As shown in FIG. 3, the sample solution storage unit 10, the tube 1, the passage 101 and the tube 2 constitute the passage system of the sample solution. The internal standard solution storage unit 30, the tube 3, the on-off valve 31, the passage 102, the tube 4 and the syringe pump 40 constitute the passage system of the internal standard solution. Moreover, the passage 103 in the mixing module 100 constitutes the communication passage of the two.

The sample solution of the sample solution storage unit 10 is transferred via the passage system of the sample solution toward the nebulizer 20 by the sucking action of a vacuum generated by the nebulizer 20. Here, the transfer of the sample solution should not be limited to the suction by the nebulizer 20 but may be exemplified by another means such as a peristaltic pump.

The internal standard solution is mixed by the syringe pump 40 into the sample solution thus transferred, via the passage 103 in the mixing module 100. The syringe pump is used to mix the internal standard solution, so that the mixing of the internal standard solution of the small quantity can be far more precisely adjusted than that of the prior art using the peristaltic pump. At this time, the on-off valve 31 is closed so that the internal standard solution is not returned to the internal standard solution storage unit 30.

On the other hand, the charge of the internal standard solution into the syringe pump 40 is so performed by opening the on-off valve 31 that the internal standard solution is sucked from the internal standard solution storage unit 30 by the syringe pump 40. Even if this suction is performed, the sample solution is not sucked together because the passage 103 in the mixing module 100 has the high passage resistance. Therefore, the internal standard solution is not contaminated with the sample solution. As a result, it is possible to omit a change-over valve or the like for preventing the contamination of the internal standard solution.

The mixing module 100 is one example of the mixing means in the present invention. The sample solution storage unit 10 is one example of the first storage means in the present invention. The nebulizer 20 is one example of the suction means in the present invention. The internal standard solution storage unit 30 is one example of the second storage means in the present invention. The on-off valve 31 is one example of the on-off valve in the present invention. The syringe pump 40 is one example of the syringe pump in the present invention.

The mixing of the internal standard solution by the syringe pump 40 is performed under the control of a controller 401. This controller 401 controls the syringe pump 40 on the basis of the detection signals of the flow rate sensors 11 and 12. As a result, even if the flow rate of the sample solution changes, the internal standard solution of a proper quantity can always be mixed while following the change.

The controller 401 further controls the ON/OFF of the on-off valve 31. The detection signals of the flow rate sensors 11 and 12 are monitored by a monitor 402 so that the suction state of the sample solution can be easily grasped. The controller 401 and the monitor 402 are included in the control module 400.

The flow rate sensors 11 and 12 are one example of the detecting means in the present invention. The controller 401 is one example of the control means in the present invention. The monitor 402 is one example of the monitor means in the present invention.

The flow rate sensors 11 and 12 are exemplified by flow rate measuring devices such as laser sensors utilizing lasers, ultrasonic sensors utilizing ultrasonic waves, electrostatic capacity sensors for detecting electrostatic capacities, or mass flow meters.

The present invention has been described by exemplifying the device for adding the internal standard solution. However, the present invention can be effectively applied to an on-line generation of a calibration curve of the standard addition method by adding a mere standard solution.

The invention claimed is:

1. A solution feeding device characterized by comprising:
    mixing means including a first passage, a second passage, and a third passage for providing communications of the midways of those two passages with a higher passage resistance than those of the two passages;
    first storage means communicating with one end side of the first passage of said mixing means for storing a sample solution;

suction means communicating with the other end side of the first passage of said mixing means for sucking the sample solution;

second storage means communicating through an on-off valve with one end side of the second passage of said mixing means for storing a standard solution; and a syringe pump communicating with the other end side of the second passage of said mixing means for sucking and discharging the standard solution, respectively, in the open state and the closed state of the on-off valve.

2. A solution feeding device as set forth in claim 1, characterized by comprising:

detecting means for detecting the flow rate of the sample solution; and control means for controlling said syringe pump on the basis of the detection signal of said detecting means.

3. A solution feeding device as set forth in claim 2, characterized by comprising monitor means for monitoring the detection signal of said detecting means.

* * * * *